United States Patent
Stammen et al.

(10) Patent No.: US 8,574,196 B2
(45) Date of Patent: Nov. 5, 2013

(54) ANESTHETIC SYRINGE HAVING A LONGITUDINALLY DISPLACEABLE FEEDING PISTON AND CHECK VALVE HAVING PASSAGE AND BLOCKING DEVICE

(75) Inventors: Christian Stammen, Kaarst-Driesch (DE); Georg Wagner, Niederzissen (DE); Olivier Georg Reinertz, Eupen (BE); Roman Josef Jansen, Wassenberg (DE)

(73) Assignee: SMJM Inject GmbH, Aachen (DE)

( * ) Notice: Subject to any disclaimer, the term of this patent is extended or adjusted under 35 U.S.C. 154(b) by 96 days.

(21) Appl. No.: 12/998,759

(22) PCT Filed: Nov. 19, 2009

(86) PCT No.: PCT/DE2009/001634
§ 371 (c)(1),
(2), (4) Date: Jul. 12, 2011

(87) PCT Pub. No.: WO2010/057473
PCT Pub. Date: May 27, 2010

(65) Prior Publication Data
US 2011/0301538 A1 Dec. 8, 2011

(30) Foreign Application Priority Data
Nov. 19, 2008 (DE) .......................... 10 2008 058 213

(51) Int. Cl.
*A61M 5/00* (2006.01)
*A61M 5/315* (2006.01)
*A61M 37/00* (2006.01)

(52) U.S. Cl.
USPC ........... 604/121; 604/143; 604/150; 604/187; 604/236

(58) Field of Classification Search
USPC ......... 604/131, 146, 150, 140–143, 121, 187, 604/236
See application file for complete search history.

(56) References Cited

U.S. PATENT DOCUMENTS

| 6,258,062 B1 * | 7/2001 | Thielen et al. ................ 604/141 |
| 7,270,648 B2 * | 9/2007 | Kazemzadeh ................ 604/135 |
| 7,717,879 B2 | 5/2010 | Mansouri |
| 2005/0070848 A1 * | 3/2005 | Kim et al. ..................... 604/140 |

FOREIGN PATENT DOCUMENTS

| DE | 196 14 337 | 8/1997 |
| WO | WO 02/49697 | 6/2002 |
| WO | WO 02/081009 | 10/2002 |
| WO | WO 2005/075009 | 8/2005 |

OTHER PUBLICATIONS

International Search Report in PCT/DE2009/001634, May 12, 2010.

* cited by examiner

*Primary Examiner* — Matthew F Desanto
(74) *Attorney, Agent, or Firm* — Collard & Roe, P.C.

(57) ABSTRACT

The invention relates to a syringe, particularly an anesthetic syringe, having a longitudinally displaceable feeding piston disposed over a first hydraulic chamber, and a second hydraulic chamber, wherein the first and second hydraulic chambers are connected by means of a first control element for regulating resistance, wherein the first control element can be actuated by a switch element, wherein the first control element comprises a first check valve.

17 Claims, 8 Drawing Sheets

Figure 1A:
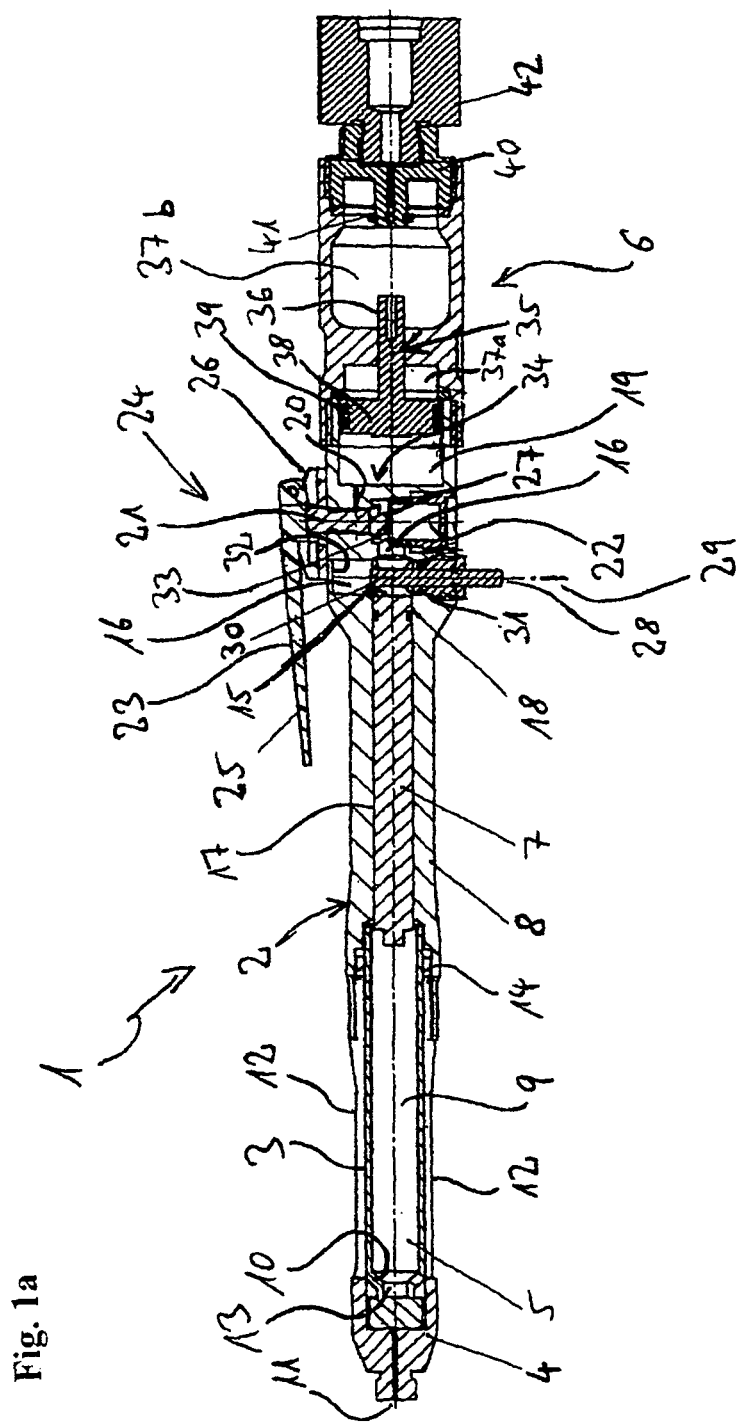

ANESTHETIC SYRINGE HAVING A LONGITUDINALLY DISPLACEABLE FEEDING PISTON AND CHECK VALVE HAVING PASSAGE AND BLOCKING DEVICE

CROSS REFERENCE TO RELATED APPLICATIONS

This application is the National Stage of PCT/DE2009/001634 filed on Nov. 19, 2009, which claims priority under 35 U.S.C. §119 of German Application No. 10 2008 058 213.1 filed on Nov. 19, 2008, the disclosure of which is incorporated by reference. The international application under PCT article 21(2) was not published in English.

The invention relates to an improved anesthetic syringe with a longitudinally displaceable feeding piston which is movably disposed above a first hydraulic chamber and with a second hydraulic chamber, the first and second hydraulic chamber being connected by means of a first control element for regulating resistance, the first control element being operable by means of a switch element.

Injecting an anesthetic agent into a human or animal body is required on a regular basis in many medical fields. Anesthetic syringes which have substantially proven efficient are used to this end.

The mostly predominant part of the anesthetic syringes used in practice is operated manually. Since this type of anesthetic syringes is widely known, there is no need to explain them.

The document WO 2005/075009 A1 provides a very handy anesthetic syringe, whereby injection processes can be carried out repeatedly and very precisely. This anesthetic syringe has a first and a second hydraulic chamber which are connected by means of one of the vertical pushers for regulating resistance or for being correspondingly controlled. In order to restore the anesthetic syringe to its initial position after an injection process, this vertical pusher must be brought back to its original position manually or correspondingly with an effort.

The object of the invention is to improve the prior art.

This object is solved by a syringe with a longitudinally displaceable feeding piston, which is movably disposed above a first hydraulic chamber, and a second hydraulic chamber, the first and second hydraulic chambers being connected via a first control element for regulating resistance, the first control element being operable via a switch element, the first control element comprising a first check valve. Medication in a carpule compartment can be introduced into a tissue by means of the feeding piston via an attached injection needle.

Resetting the syringe can thus occur advantageously without actuating a release lever, since the check valve opens independently, thus allowing the hydraulic fluid to be fed from the first hydraulic chamber into the second hydraulic chamber.

Check valves of the type mentioned here can more specifically comprise standard check valves which can be acquired as prefabricated components. The manufacturing price of such a syringe can thereby be advantageously reduced.

In an embodiment of the invention a resistance element can be connected in series with the first check valve between the first and second hydraulic chamber and thus more specifically comprise the first control element, a first check valve and a resistance element. A resistance can thus be advantageously adjusted, so that the injection proceeds in a manner that is more homogenous and more comfortable for the patient.

The resistance element can be configured as a throttle or baffle.

When a resistance element according to paragraph 9 is included, a second control element, more specifically a second check valve, can be connected in parallel to the first control element between the first and second hydraulic chamber, in order to bring the feeding piston back to its original position after an injection process with as little effort as possible. Thus, in case of a manual actuation of the feeding piston, the hydraulic fluid can flow from the first hydraulic chamber to the second hydraulic chamber via the second control element without the increased flow resistance of the first control element becoming noticeable.

In an embodiment of the invention, the switch element can be configured as a pin or correspondingly as an actuating pin which is displaceable and which opens the first control element when actuated, so that the first and second hydraulic chambers are conductively connected to each other. An easy actuation of the control element can thus occur advantageously.

In order for the person actuating the syringe to get a feeling for the pressure in the carpule, the switch element can have an active surface which transfers at least a part of the hydraulic pressure acting in the syringe and thus of an acting force to the user by means of the switch element/control member.

In another embodiment of the invention, the acting force can be amplified. This can more specifically be advantageous if a force which the actuating person barely feels is sufficient for actuating the control element, but which the actuating person can then haptically detect via the active surface. In order to feed this force back to the user via a switch system, the amplification of the acting force can be advantageously implemented via another pin with the action of a force via a lever.

In another embodiment of the invention, the amplification of the force can occur via a lever system of two levers connected to each other. The lever arm which actuates the pin of the switch element/control member is thereby located close to the fulcrum or correspondingly to the lever axis of the second lever. The second lever is ideally actuated at the end of the second lever arm.

In order to implement a resistance element, the resistance element can be configured as a gap with a gap length around the switch element, more specifically the pin. The hydraulic fluid thereby flows around the pin along the gap which acts as a resistance for the hydraulic fluid which flows from the first hydraulic chamber to the second hydraulic chamber.

In another embodiment of the invention, the gap length can be configured in such a manner that the gap length changes when actuating the switch element. Thus, a non-constant resistance can be advantageously implemented.

In order to fill a gas compartment, which serves more specifically to provide the energy in the syringe, the syringe can comprise a gas compartment which is connected to the second hydraulic chamber via a movable separation piston or a membrane, wherein this gas compartment can be filled via a filling nozzle, the gas compartment being sealed relative to the filling nozzle by means of an O-ring, the O-ring being configured in such a manner that it develops the function of a check valve. An easy filling of the gas compartment can be advantageously implemented in this embodiment, the gas compartment being substantially hermetically sealed after being filled.

The O-ring mentioned here, as well as all the other O-rings mentioned in this document can pretension seals which are more specifically configured as rings and thus form a sliding seal system made of an O-ring and a tensioned seal.

In order to prevent an introduction of gas into the hydraulic fluid in the second hydraulic chamber, the separation piston can form a piston system with two sealing elements which respectively seal the gas compartment and the second hydraulic chamber, the piston system being guidable along a limiting element, the sealing elements, the separation piston and the limiting system forming a cavity which has an aperture onto the environment.

The syringe is advantageously configured in such a manner that the aperture forms an exchange contact between the cavity and the environment in all positions of the separation piston. The introduction of gas into the hydraulic fluid can thereby be advantageously prevented in all positions of the piston.

In another embodiment of the invention, the second hydraulic chamber can be completely separated by an independent, completely self-contained gas tank which is connected to the second hydraulic chamber, whereby an introduction of gas into the second hydraulic chamber can be advantageously prevented.

The independent, completely self-contained gas tank can be configured as a collapsible piston element, the piston element being highly deformable along the main movement axis of the syringe and hardly deformable radially, the gas compartment being adapted to be filled by means of a filling nozzle, the gas compartment inside the piston element being sealed relative to the filling nozzle by means of an O-ring, the O-ring being configured in such a manner that it develops the function of a check valve. An easy filling of the gas compartment can be implemented by means of this embodiment, the gas compartment being substantially hermetically sealed after filling.

This O-ring can more specifically be further developed in such a manner that a sliding seal element is formed with it, which supersedes the O-ring.

Such type collapsible piston elements can more specifically comprise spring type accumulators which are acquirable as a prefabricated component.

In order to vent the completely closed gas tank as required, a closable venting aperture can be integrated, the venting being configured in such a manner that the venting of the gas compartment preferably occurs before the separation of the gas tank from the second hydraulic chamber. A safe separation of the gas tank from the second hydraulic chamber can be implemented advantageously by means of this embodiment.

In another aspect of the invention, a check valve can be implemented, the check valve forming a forward and a reverse direction, the check valve connecting a first and a second compartment, the check valve being formed by means of an O-ring which surrounds a groove. The groove thereby has a connection to the first compartment, and the O-ring is located substantially in the second compartment. The O-ring thus seals the second compartment relative to the first compartment, provided the second compartment has a higher pressure than the first compartment. In case the first compartment has a higher pressure than the second compartment, the O-ring expands and a conductive connection from the first to the second compartment is formed. A fluid can thus be conducted from the first to the second compartment.

The O-ring mentioned here can also be more specifically developed in such a manner that a sliding seal system is formed with it which supersedes the O-ring.

Such type O-rings and sliding seal systems can comprise all sealing elements which seal a compartment relative to another one as a result of their elasticity, in which the tensioned rings of the sliding seal systems can comprise PTFE, FKM and FFKM. The materials FKM (fluororubber), and FFKM more specifically can be used in systems, in which the pre-tensioned rings are exposed to a chemically aggressive environment. The pre-tensioned rings of the company Trellborg which are listed under the registered trade names Turcon, Stepseal 2K and/or Zurcon can more specifically be used.

In an embodiment of the invention, the O-ring can be configured so that it is expandable radially outward in the forward direction and that it can perform the function of a seal in the reverse direction. Standard O-rings such as those available in commerce can thus be used advantageously.

In another aspect of the invention, an O-ring is used as a check valve.

The invention is explained in the following by means of exemplary embodiments.

Figure 1B:
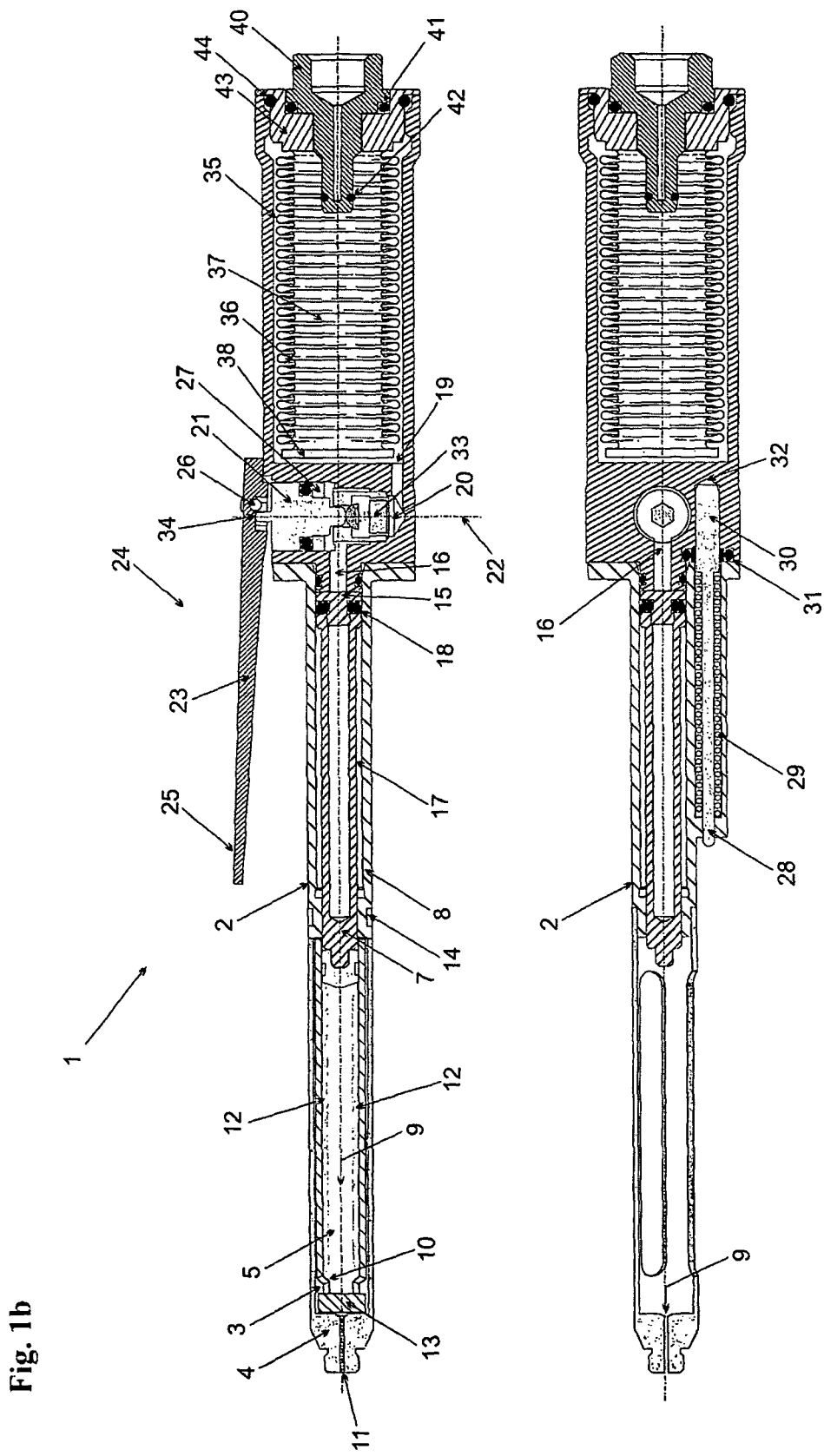
Figure 1C:
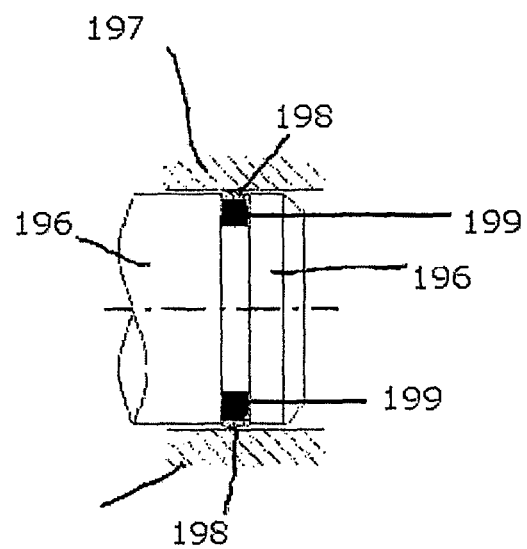
Figure 2:
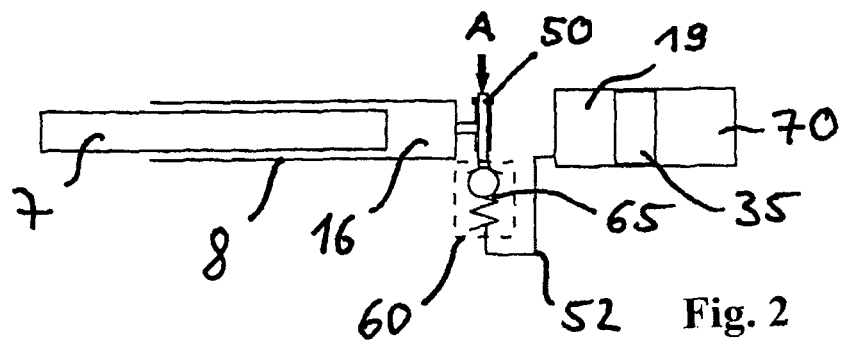
Figure 3:
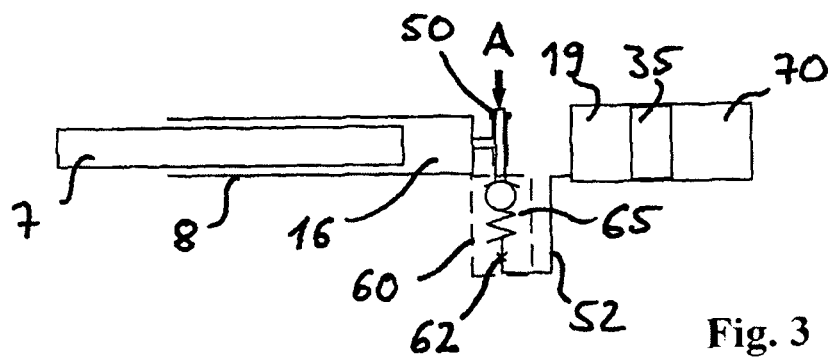
Figure 4:
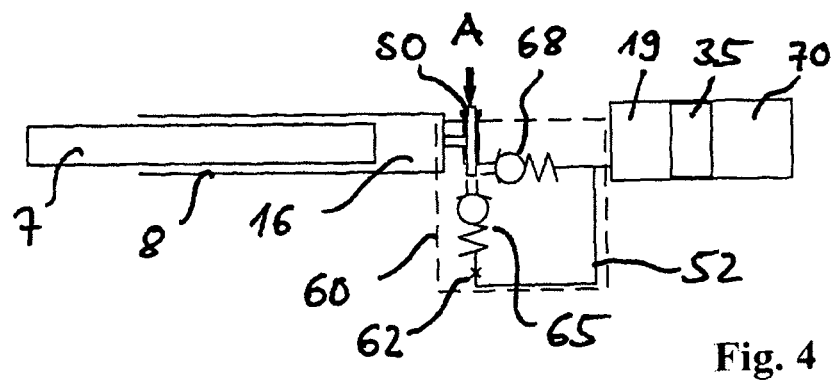
Figure 5:
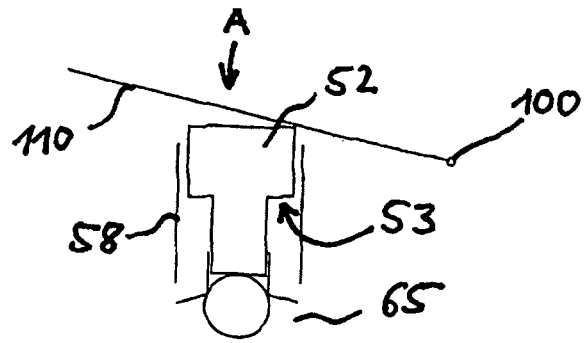
Figure 6:
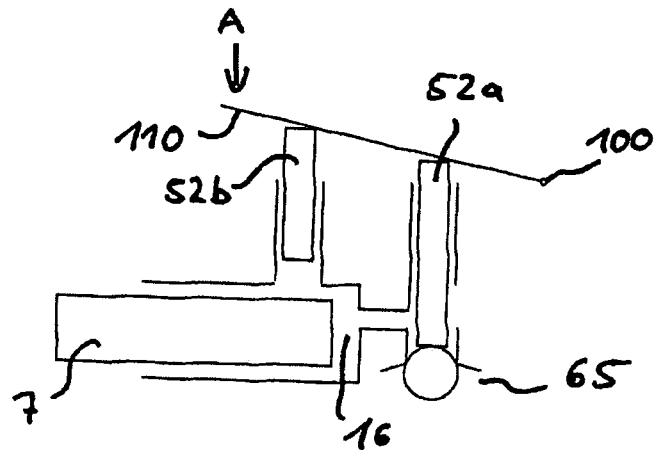
Figure 7:
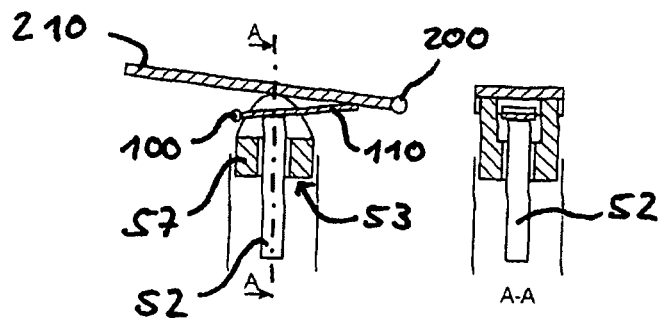
Figure 8:
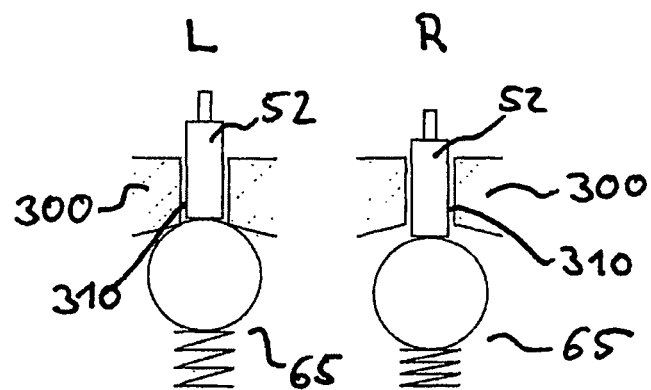
Figure 9:
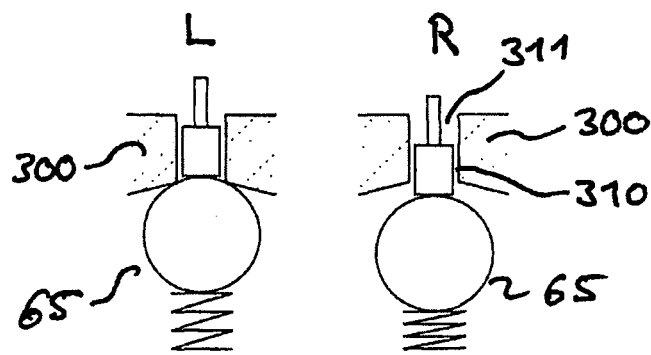
Figure 10:
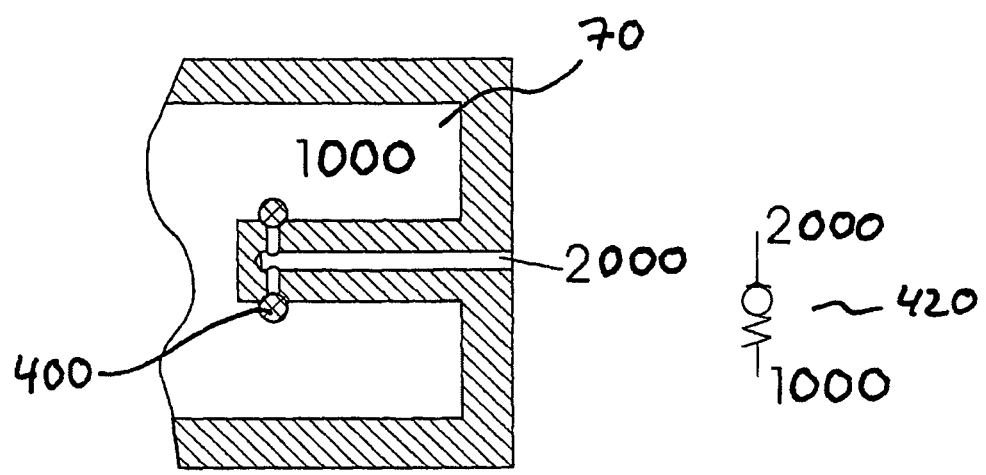
Figure 11:
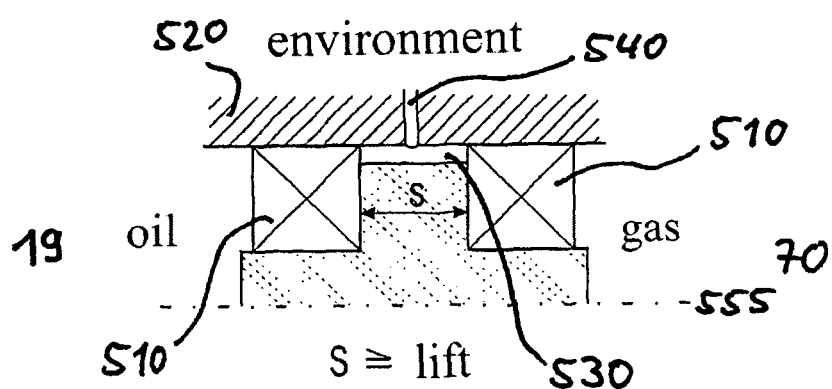

In the drawings:

FIG. 1a an anesthetic syringe with a serial disposition of a carpule compartment, a feeding piston, a first hydraulic chamber, a second hydraulic chamber, a separation piston and a pressure compartment, FIG. 1b an anesthetic syringe with a serial disposition of a carpule compartment, a feeding piston, a first hydraulic chamber, a second hydraulic chamber and a gas compartment, a membrane bellow being disposed in the gas compartment, FIG. 1c a sliding system, in which an O-ring pretensions a PTFE-ring, FIG. 2 a syringe with a first and a second hydraulic chamber, which are connected via a check valve, FIG. 3 a syringe with a first and second hydraulic chamber which are connected via a check valve, a resistance element being disposed between the check valve and the second hydraulic chamber, FIG. 4 the syringe from FIG. 3, which is upgraded by a second control element, FIG. 5 a pin with an active surface which actuates the control element via a lever, FIG. 6 a system in which the acting forces are amplified, FIG. 7 a lever system with two levers connected to each other, FIG. 8 a switch element with a gap and a gap length along the entire control area, FIG. 9 a gap length which changes when actuating the switch element, FIG. 10 an O-ring as check valve and the associated equivalent circuit, FIG. 11 a venting device in the syringe.

The anesthetic syringe 1 in FIG. 1a consists substantially of a casing 2, which can receive a carpule 5 in a carpule compartment 3 of a carpule hull 4 and expel its content by means of a hydraulic-pneumatic drive system 6 via a feeding piston 7.

The feeding piston 7 is movably mounted in a feeding cylinder 8 along a main extension axis 9 of the anesthetic syringe 1, the feeding piston 7 taking up an inner end position in the figure and being movable during a feeding motion along the axis 9 up to a stop shoulder 10 where it adopts an outer end position. During the feeding motion, the feeding piston 7 runs through the carpule compartment 3, so that fluid from an inserted carpule 5 can be sprayed out through a needle aperture 11. A cannula is introduced into the needle aperture 11 for using the syringe 1. The cannula has a point for penetrating a tissue and a second point for penetrating the sealing membrane of the inserted carpule 5.

A special adaptor for the cannula is provided in the needle aperture 11 (not shown in detail), in order to prevent an accidental insertion of a cannula into the syringe 1 which would mechanically fail under sometimes high pressures.

The carpule hull 4 has two inspection windows 12 through which the feeding position of the feeding piston 7 inside the carpule hull 4 is visible. The carpule 5 has a head configuration 13 which is customary in the trade, so that the attending doctor is not limited in his choice of the carpules which he already knew from his work with customary syringes. The carpule hull 4 is solidly connected to the feeding cylinder 8 via a bayonet catch 14.

The pressure plate 15 of the feeding piston 7 faces a first hydraulic chamber 16, a lateral surface 17 of the feeding piston 7 being sealed relative to the first hydraulic chamber 16 via an O-ring 18.

A second hydraulic chamber 19 is provided rearward from the first hydraulic chamber 16 and is connected to the first hydraulic chamber 16 via a control bore 20. The opening of the control bore 20 between the first hydraulic chamber 16 and the second hydraulic chamber 19 is controlled by a valve slide 21, which is movably located along a motion direction 22 and abuts against a button arm 23 of a control button 24. The control button 24 has a touch surface 25 for depressing the button arm 23—and thus the valve slide 21. The button arm 23 is rotatably mounted around a button bolt on a button bearing 26 for this. The button bolt lies perpendicularly to the main extension axis 9 of the anesthetic syringe 1.

The valve slide 21 extends with a pressure plate 27 into the first hydraulic chamber, whereas the lateral surface of the valve slide 21 is sealed by an O-ring.

An index piston 28 is mounted in a similar way in the casing 2 along a direction 29 which is radial relative to the main extension direction 9 of the syringe 1. The index piston 28 extends with a piston base 30 into the first hydraulic chamber 16, whereas the lateral surface of the index piston 28 is sealed by an O-ring 31. A pressure spring (not shown) presses the index piston 28 to an inner end position in which the base 30 comes to rest on an inner limiting surface 32 (in the figure, the index piston 28 is shown in an extension up to a limit stop for greater clarity; however, in the present embodiment 1, without pressure in the hydraulic chamber 1, the index piston takes up the inner end position in practice).

In an idle state, another pressure spring 33 presses the pre-tensioned valve slide 21 into the shown outer end position which is defined by a pressure plate 27 with an augmented configuration relative to the cylindrical part of the slide 21, coming to rest on a limit stop 34 on the casing 2.

The second hydraulic chamber 19 is delimited rearward by a separation piston 35 which is movably mounted along the main extension axis 9 of the syringe 1 and which in turn protrudes rearward into a pressure compartment 37a, 37b and thereby delimits it. A pressure plate 28 constitutes the essential element of the separation piston 35. A double O-ring seal 39 is provided on sides of the pressure plate 38. In order for the separation piston 35 to not get jammed between the second hydraulic chamber 19 and the pressure compartment 37a during motion, a guide for a cylindrical guide bar 36 of the separation piston 35 is provided in the pressure compartment 37, 37b. Big apertures connect both partial compartments 37a and 37b of the pressure compartment (not shown in the figure)

The pressure compartment 37b is delimited rearward by a closing plug 40 which is hermetically connected to the pressure compartment 37 via another O-ring 41 and is equipped with a check valve (not shown in detail) via which a gas cartridge or an adapter 42 for connecting a compressed gas duct is connected to the syringe 1.

During operation, the hydraulic pressure required for the feeding motion of the feeding piston 7 is generated by the pressure compartment 37. The separation piston 35 thereby separates the gas volume (filled under pressure into the pressure compartment 37 via the adapter 42) from the hydraulic oil in the second hydraulic chamber 19. The pressurized hydraulic oil can reach the valve slide 21 via the control bore 20. In an idle state, the valve slide is closed by the pressure spring 33. The pressure spring is pre-tensioned by means of a screw cap (not labeled, disposed in the casing 2 on the side opposite to the valve slide 21 along its extension), in order to generate the necessary sealing force at the control bore 20. The valve is a proportional 2/2-way seat valve; depending on the valve lift, the volume flow and thus the extension speed of the feeding piston 7 can thus be controlled.

In order to extend the feeding piston 7, the button arm 23 must be actuated, preferably at its touch surface 25, in the direction of the casing 2 of the syringe 1. The valve slide 21 is thereby necessarily displaced along its motion direction 22 against the pressure spring 23 into the casing 2 of the syringe 1. The hydraulic oil can now flow through the freed flow cross-section from the second hydraulic chamber 19 to the first hydraulic chamber 16. The piston head 15 of the feeding piston 7 is thus impinged with a force, so that the feeding piston 7 extends.

If an opposing force rests against the feeding piston 7 via the tissue in which the syringe 1 has been inserted, the pressure increases in both hydraulic chambers, but more specifically in the first hydraulic chamber 16 due to hydraulic losses at the control bore 20. This pressure acts onto the base 27 of the slide valve 21 in the closing direction of the valve. The attending doctor feels the changed pressure via the button 24 and has to correspondingly press stronger onto the button 24, in order for the valve slide 21 to remain in an opened position and in order for the valve of the control bore 20 to remain open.

In addition to this sensing of the pressure, an optical pressure display is also available via the index piston 28 which displays the cylinder pressure and thus the piston force—which can be viewed as a measure for the pressure of the injection. The index piston 28 thereby serves as a small single-acting hydraulic cylinder, on the piston of which three grooves are inserted for displaying the amount of pressure. In the idle state, the piston 28 is maintained in the casing 2 by the spring (this state is not shown here). With an increase of the hydraulic pressure in the first hydraulic chamber, a force is generated via the base 30 of the index piston 28, which counteracts the pretension of the spring and, according to the hydraulic pressure conditions in the first hydraulic chamber 16, extends the index piston 28 to a greater or lesser extent out of the casing 2 of the syringe 1 along the motion direction 29. The pressure can then be read via the grooves on the piston 28.

If the feeding piston 7 is completely extended and the glass carpule 5 is thus emptied, a new glass carpule must be inserted into the carpule hull 4 for the next treatment. To this end, the carpule hull 4 is separated from the casing 2 of the syringe 1 via the bayonet catch, the carpule is changed and the carpule hull is subsequently connected back to the feeding cylinder 8 via the bayonet catch.

The feeding piston 7 must additionally be brought back to its inner end position. To this end, the syringe 1 must be inserted into a charging station and the feeding piston 7 must be pushed back via a lever mechanism. To this end, the charging station actuates the button arm 23 and opens the valve of the control bore 20, in order to establish a connection between the first 16 and the second hydraulic chamber 19. As the feeding piston 7 is pushed back, the separation piston 35 moves back to the inner end position and pressurizes the gas volume in the pressure compartment 37 back to the original pressure.

The figure shows the filling adapter 42 for a potentially necessary re-filling or for a first filling of the syringe with the spring gas. The pressure compartment 37 can be filled with pressurized nitrogen via this adapter. The check valve at the O-ring 41 thereby prevents an outflow of the gas when the adapter is unscrewed.

The further numbering refers to the exemplary embodiment of FIG. 1b.

The anesthetic syringe 1 in FIG. 1b consists substantially of a casing 2 which can receive a carpule 5 in a carpule compartment 3 of a carpule hull 4 and expel its content by means of a hydraulic-pneumatic drive system 6 via a feeding piston 7.

The feeding piston 7 is movably mounted in a feeding cylinder 8 along a main extension axis 9 of the anesthetic syringe 1, the feeding piston 7 taking up an inner end position in the figure and being movable during a feeding motion along the axis 9 up to a stop shoulder 10 where it adopts an outer end position. During the feeding motion, the feeding piston 7 runs through the carpule compartment 3, so that fluid from an inserted carpule 5 can be sprayed out through a needle aperture 11. A cannula is introduced into the needle aperture 11 for using the syringe 1. The cannula has a point for penetrating a tissue and a second point for penetrating the sealing membrane of the inserted carpule 5.

A special adaptor for the cannula is provided in the needle aperture 11 (not shown in detail), in order to prevent an accidental insertion of a cannula into the syringe 1 which would mechanically fail under sometimes high pressures.

The carpule hull 4 has two inspection windows 12 through which the feeding position of the feeding piston 7 inside the carpule hull 4 is visible. The carpule 5 has a head configuration 13 which is customary in the trade, so that the attending doctor is not limited in his choice of the carpules which he already knew from his work with customary syringes. The carpule hull 4 is solidly connected to the feeding cylinder 8 via a bayonet catch 14.

The pressure plate 15 of the feeding piston 7 faces a first hydraulic chamber 16, a lateral surface 17 of the feeding piston 7 being sealed relative to the first hydraulic chamber 16 via a sliding seal system 18.

A second hydraulic chamber 19 is provided rearward from the first hydraulic chamber 16 and is connected to the first hydraulic chamber 16 via a control bore 20. The opening of the control bore 20 between the first hydraulic chamber 16 and the second hydraulic chamber 19 is controlled by a valve slide 21 via a check valve 13, the valve slide 21 being movably mounted along a motion direction 22 and abuts against a button arm 23 of a control button 24 on an outer side of the casing 2.

The control button 24 has a touch surface 25 which faces the front area of the syringe 1 for depressing the button arm 23—and thus the valve slide 21. To this end, the button arm 23 is rotatably mounted around a button bolt on a button bearing 26. The button bolt lies perpendicularly to the main extension axis 9 of the anesthetic syringe 1.

The valve slide 21 extends with a pressure plate 27 into the first hydraulic chamber, while the lateral surface of the valve slide 21 is sealed by a sliding seal system.

An index piston 28 is mounted in a similar way in the casing 2 along the main extension direction 9 of the syringe 1. The index piston 28 extends with a piston base 30 into the first hydraulic chamber 16, while the lateral surface of the index piston 28 is sealed by a sliding seal system 31. A pressure spring 29 presses the index piston 28 to an inner end position in which the base 30 comes to rest on an inner limiting surface 32.

In an idle state, a pressure spring 33 presses the pre-tensioned valve slide 21 into the shown outer end position which is defined by a pressure plate 27, with an augmented configuration relative to the cylindrical part of the slide 21, coming to rest on a limit stop 34 on the casing 2.

The second hydraulic chamber 19 is delimited rearward by a gas tank 35 which is configured so as to be deformable along the main extension axis 9 of the syringe 1 and which in turn forms a self-contained pressure compartment 37 and thereby delimits it. A metal bellow 36 which is deformable in an accordion-like manner along the main extension axis 9 constitutes the essential element of the gas tank 35, the gas tank 35 being closed in the direction of the second hydraulic chamber 19 by a cover plate 38 and rearward by a tank cover 43, whereby a pressure compartment 37 is formed which is completely separated from the hydraulic oil and free of movable sealing elements. The gas tank 35 is connected by the tank cover 43 to the second hydraulic chamber 19 via an O-ring 44.

The pressure compartment 37 is delimited rearward by a closing plug 40 which is hermetically connected to the pressure compartment 37 via another O-ring 41 and is equipped with a check valve 42 via which a gas cartridge or an adapter for connecting a compressed gas duct is connected to the syringe 1.

During operation, the hydraulic pressure required for the feeding motion of the feeding piston 7 is generated by the pressure compartment 37. The gas compartment 35 thereby separates the gas volume (filled under pressure into the pressure compartment 37 via the closing plug) from the hydraulic oil in the second hydraulic chamber 19. The pressurized hydraulic oil can reach the valve slide 21 via the control bore 20. In an idle state, the valve slide is closed by the check valve 33. The check valve 33 is disposed in series with the second hydraulic chamber 19 in the reverse direction, in order to generate the necessary sealing force at the control bore 20. The valve is a proportional seat valve; depending on the valve lift, the volume flow and thus the extension speed of the feeding piston 7 can thus be controlled.

In order to extend the feeding piston 7, the button arm 23 must be actuated, preferably at its touch surface 25, in the direction of the casing 2 of the syringe 1. The valve slide 21 is thereby necessarily displaced along its motion direction 22 against the pressure spring of the check valve 33 into the casing 2 of the syringe 1. The hydraulic oil can now flow through the freed flow cross-section from the second hydraulic chamber 19 to the first hydraulic chamber 16. The piston head 15 of the feeding piston 7 is thus impinged with pressure, so that the feeding piston 7 extends.

If an opposing force rests against the feeding piston 7 via the tissue in which the syringe 1 has been inserted, the pressure increases in both hydraulic chambers, but more specifically in the first hydraulic chamber 16 due to hydraulic losses at the control bore 20. This pressure acts onto the base 27 of the slide valve 21 in the closing direction of the valve. The attending doctor feels the changed pressure via the button 24 and has to correspondingly press stronger onto the button 24, in order for the valve slide 21 to remain in an opened position and in order for the valve of the control bore 20 to remain open.

In addition to this sensing of the pressure, an optical pressure display is also available via the index piston 28 which displays the cylinder pressure and thus the piston force—which can be viewed as a measure for the pressure of the injection. The index piston 28 thereby serves as a small single-acting hydraulic cylinder, on the piston of which three grooves for displaying the amount of pressure are inserted. In the idle state, the piston 28 is maintained in the casing 2 by the spring 29.

With an increase of the hydraulic pressure in the first hydraulic chamber, a force is generated via the base 30 of the index piston 28, which counteracts the pretension of the spring and, according to the hydraulic pressure conditions in the first hydraulic chamber 16, extends the index piston 28 to a greater or lesser extent out of the casing 2 of the syringe 1 along the motion direction 9. The pressure can then be read via the grooves on the piston 28.

If the feeding piston 7 is completely extended and the glass carpule 5 is thus emptied, a new glass carpule must be inserted into the carpule hull 4 for the next treatment. To this end, the carpule hull 4 is separated from the casing 2 of the syringe 1 via the bayonet catch, the carpule is changed and the carpule hull 4 is subsequently connected back to the feeding cylinder 8 via the bayonet catch.

The feeding piston 7 must additionally be brought back to its inner end position. To this end, the syringe 1 must be inserted into a charging station and the feeding piston 7 must be pushed back via a lever mechanism. The check valve 33 is hereby opened and a connection between first 16 and the second hydraulic chamber 19 is thus established. As the feeding piston 7 is pushed back, the gas tank 35 is compressed and the gas volume in the pressure compartment 37 is pressurized back to the original pressure.

An adapter for a potentially necessary re-filling after several uses or for a first filling of the syringe with the spring gas is connected to the filling plug 40. The pressure compartment 37 can be filled with pressurized nitrogen via this adapter. The check valve at the O-ring 42 thereby prevents an outflow of the gas when the adapter is unscrewed.

FIG. 1c shows a sliding seal system, a piston 196 and a cylinder 197. The sliding seal system comprises the O-ring 199 and a ring 198 made of PTFE, the O-ring 100 pretensioning the ring made of PTFE. Due to its elasticity and the associated restoring force, the O-ring 199 presses the PTFE ring 198 against the wall of the cylinder 197. The piston 196 can thus be guided in the cylinder 197 in such a manner that compartments forming on the left and right hand side of the slide seal system are sealed relative to each other.

FIGS. 2, 3 and 4 describe three possibilities for using a check valve in a syringe. FIG. 2 shows a variant with a check valve 65. The check valve 65 which is used here instead of the vertical slide 21, is used for controlling the syringe 1 in that the sealing body of the valve (shown here as a ball) is displaced against the spring force by means of an actuating pin or a pin 50 in the direction A and that a control cross-section is thus freed.

A pressure can now be generated in the first hydraulic chamber 16 via the control cross-section via the second hydraulic chamber 19. This is implemented via the duct 52 and the control element 60, which is shown separately here since it is a component which is customary in the trade. The gas pressure in the gas tank 70 can generate a pressure in the second hydraulic chamber via the separation piston 35, this pressure driving the feeding piston 7 into the carpule compartment 3 via the second and first hydraulic chambers when actuating the control element.

FIG. 3 shows a variant with a check valve 65 and a throttle 62 which acts as a resistance element. The throttle 62 can be disposed here before (as shown here) as well as after the check valve 65. An improved dosing can be achieved by means of this embodiment. A baffle can also be used as a resistance element instead of a throttle. These elements can also be configured in such a manner that the user modifies the resistance element. This can be implemented more specifically by an adjusting screw which constricts the feeding pipe 60.

FIG. 4 shows a variant with two check valves and a throttle 62. As compared to FIG. 3, the second check valve 68 which takes up the function of the second control element here, is connected to the first and second hydraulic chamber and thus implements a parallel connection of the second control element 68 and the first control element 65 with the throttle 62 connected in series with the first control element 65.

FIGS. 5 and 7 show three actuation possibilities for opening the check valve and for the feedback of the force to the user. In FIG. 5, the pin 52 has a circumferential annular surface 53 which is configured as an active surface; the switch element thus comprises a pin 52 with an active surface 53 and a check valve 65, the pin being substantially led through the guiding means 58. The switch element can be moved or correspondingly switched by actuation in the direction A via the lever 110 which rotates around the fulcrum or correspondingly around the lever axis 100.

FIG. 6 shows an active surface which is spatially separated from the first pin 52a. The switch element comprises the first pin 52a which can act on the check valve 65 and the second pin 52b which receives the force feedback via the first hydraulic chamber 16 and the lever 110 which is led around the fulcrum (lever axis) 100. The required force on the actuating pin has the same magnitude as the feedback force but must not be felt by the user since it impairs the haptic detection of the acting pressure. The actuation is therefore disposed closely to the lever axes.

In order to reinforce the feedback force, the second pin 52b is located further away from the fulcrum (lever axis) 100 than the first pin 52a. The pin 52a as well as the pin 52b are both actuated via a common lever(arm) 110. If the hydraulic fluid flows into the first hydraulic chamber 16 when the lever 110 is actuated, the pressure which is generated in the hydraulic chamber is transferred to the second pin 52b. This force is transferred on the lever 100 to the user.

Two separate but coaxial feedback surfaces with a lever system are shown in FIG. 7. The right hand part of the figure shows the viewing direction A-A. The inner pin 52 serves for opening the check valve (not shown), the ring surface 53 serves for a pressure-dependent force feedback. The actuation of the pin 52 occurs by means of a first lever 110, 100 which is coupled to the second lever 210, 220. Different lever transmissions for two coaxially disposed components are thus achieved. The lever axes are respectively attached in a fixed position in the casing.

The FIGS. 8 and 9 show implementations of resistance elements. The non-actuated check valve is shown on the left hand side L and the actuated check valve is shown on the right hand side R.

FIG. 8 shows a resistance element with a constant resistance. A gap 310 located between the actuating pin 52 and the check valve casing 300 serves for throttling. By actuating the pin 52, the length and height of the throttle gap 310 is not changed. The throttling action is thus constant along the lift.

FIG. 9 shows a throttle with a changeable position along the lift which leads to a change of the resistance. The left and right hand sides again show the switch element in the actuated and non actuated state. A change of the length of the throttle gap, which is implemented by the narrowing cross-section of the pin, leads to a lift-dependent throttle action which can be used for dosing. A non-constant resistance is thus implemented.

FIG. 10 shows the gas tank 70 which is separated from the filling nozzle 2000 via an O-ring 400, the gas tank 70 acting here as a first compartment 1000 and the filling nozzle as a second compartment 2000. If a gas cartridge for instance is flanged onto the filling nozzle, the pressure in the second compartment 2000 can exceed the pressure in the first compartment 1000. The elastic element 400, which is configured here as an O-ring, thereby expands and the pressure in the first compartment 1000 increases. Regarding the mode of action, the equivalent circuit 420 is shown on the right hand side as a check valve.

In order to prevent a gas from entering a fluid, such as hydraulic oil, a device such as shown in FIG. 1 in a sectional view is provided. The passage from the gas compartment 70 to the second hydraulic chamber 19 comprising oil is thereby shown. The seals 510 respectively seal the systems from one another via the piston 35. The lift of the piston is labeled S. An empty compartment (intermediary compartment) 530 is formed between the piston and the limit 520. This intermediary compartment has an opening 540 into the environment. A venting of the gas which reached the gap through the seal can be implemented via this opening.

The invention claimed is:

1. A syringe, more specifically an anesthetic syringe with a longitudinally displaceable feeding piston which is movably disposed above a first hydraulic chamber and with a second hydraulic chamber, the first and second hydraulic chambers being connected via a first control element for regulating resistance, the first control element being operable via a switch element, and the switch element being an actuating pin, wherein the actuating pin is assigned to a first check valve, so that the first check valve can be actuated via the actuating pin, and
   wherein the syringe is configured to provide a feedback force to a user via an amplification of the acting force, the amplification being implemented via another pin with the action of a force via a lever.

2. The syringe according to claim 1, the syringe comprising a gas compartment which is connected to the second hydraulic chamber.

3. The syringe according to claim 2, the gas compartment being connected to the second hydraulic chamber via an expandable, more specifically completely closed gas tank, more specifically a membrane bellow which acts as a spring membrane tank.

4. The syringe according to claim 3, the gas tank being adapted to be filled via a filling nozzle.

5. The syringe according to claim 3, the expandable gas tank having a closable venting aperture and the venting of the gas tank occurring before the separation of the gas tank from the second hydraulic chamber.

6. The syringe according to claim 2, the gas compartment being adapted to be filled via a filling nozzle and the gas compartment being sealed relative to the filling nozzle via an O-ring, the O-ring being configured in such a manner that it develops the function of a check valve.

7. The syringe according to claim 2, a connection of the gas compartment and the second hydraulic chamber occurring via a movable separation piston.

8. The syringe according to claim 1, a resistance element being connected in series with the first check valve between the first and second hydraulic chamber and thus more specifically comprises the first control element, a first check valve and a resistance element.

9. The syringe according to claim 1, the resistance element being configured as a throttle or a baffle.

10. The syringe according to claim 1, a second control element, more specifically a second check valve, being connected in parallel to the first control element between the first and second hydraulic chamber.

11. The syringe according to claim 1, the switch element comprising a pin which is displaceable and which opens the first control element when actuated, so that the first and second hydraulic chamber are conductively connected to each other.

12. The syringe according to claim 1, the switch element comprising an active surface which transfers at least a part of a hydraulic pressure and thus of an acting force via the control member.

13. The syringe according to claim 1, the resistance element being configured as a gap with a gap length around the switch element, more specifically the pin.

14. The syringe according to claim 1, the gap length being configured in such a manner that the gap length changes when actuating the switch element.

15. The syringe according to claim 1, the separation piston and two sealing elements which respectively seal the gas compartment and the second hydraulic chamber, forming a piston system, the piston system being guidable along a limiting element, the sealing elements, the separation piston and the limiting system forming a cavity which implements an aperture onto the environment.

16. The syringe according to claim 1, the aperture forming an exchange contact between the cavity and the environment in all positions of the separation piston.

17. A syringe, more specifically an anesthetic syringe with a longitudinally displaceable feeding piston which is movably disposed above a first hydraulic chamber and with a second hydraulic chamber, the first and second hydraulic chambers being connected via a first control element for regulating resistance, the first control element being operable via a switch element, and the switch element being an actuating pin, wherein the actuating pin is assigned to a first check valve, so that the first check valve can be actuated via the actuating pin, and wherein an amplification of the force occurs via a lever system of two levers connected to each other.

\* \* \* \* \*

UNITED STATES PATENT AND TRADEMARK OFFICE
CERTIFICATE OF CORRECTION

PATENT NO.       : 8,574,196 B2                                          Page 1 of 1
APPLICATION NO. : 12/998759
DATED            : November 5, 2013
INVENTOR(S)      : Stammen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

Signed and Sealed this
Twenty-second Day of September, 2015

Michelle K. Lee
*Director of the United States Patent and Trademark Office*